United States Patent [19]

Ito et al.

[11] 4,040,742
[45] Aug. 9, 1977

[54] CAPILLARY FLOW METHOD AND APPARATUS FOR DETERMINATION OF CELL OSMOTIC FRAGILITY

[75] Inventors: Yoichiro Ito, Bethesda; Peter Carmeci, Potomac, both of Md.

[73] Assignee: The United States of America as represented by the Secretary of the Department of Health, Education and Welfare, Washington, D.C.

[21] Appl. No.: 713,045

[22] Filed: Aug. 9, 1976

[51] Int. Cl.² .................. G01N 33/16; G01N 21/26
[52] U.S. Cl. ........................... 356/39; 73/53; 210/65; 356/40; 356/181; 356/208
[58] Field of Search .................. 356/36-37, 356/39-42, 181, 201, 208; 73/53; 210/65, 511

[56] References Cited

U.S. PATENT DOCUMENTS

| | | | |
|---|---|---|---|
| 3,300,385 | 1/1967 | Danon | 356/40 |
| 3,334,018 | 8/1967 | Smythe | 23/230 B |
| 3,606,539 | 9/1971 | Polanyi et al. | 73/53 |

OTHER PUBLICATIONS

Kitazima et al. "Coil Planet Centrifugation & its Application to the Observation of Altered Membrane Properties of Erthrocytes in Hepatobiliary Disorders", J. Lab. Clin. Med., May 1975, pp. 855-864.

*Primary Examiner*—John K. Corbin
*Assistant Examiner*—Wm. H. Punter
*Attorney, Agent, or Firm*—Browdy and Neimark

[57] ABSTRACT

A method and apparatus for the determination of blood cell osmotic fragility, wherein a solution of salt, such as sodium chloride, with an osmotic gradient decreasing with time is passed through a coiled capillary tube, positioned with its axis vertical so that the flow through the turns of the tube is substantially horizontal. and the flow follows Poiseuille's parabolic flow pattern. The blood sample is inserted in the coiled tube and, because of the flow pattern, the salt solution travels through the capillary tube much faster than the erythrocytes, so that the erythrocytes are exposed to gradually decreasing osmolarity for hemolysis. Optical monitoring is carried out as the hemoglobin is rapidly removed from the flowing stream. Optical density is recorded against time, employing a 547 nm monitoring beam, thus providing a hemolysis curve.

13 Claims, 6 Drawing Figures

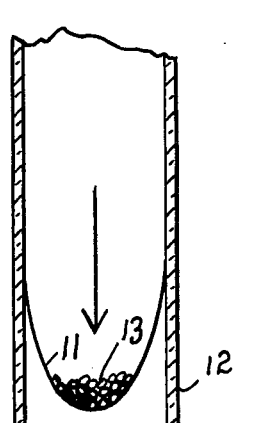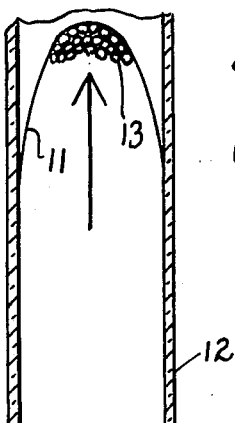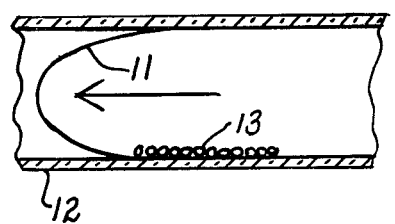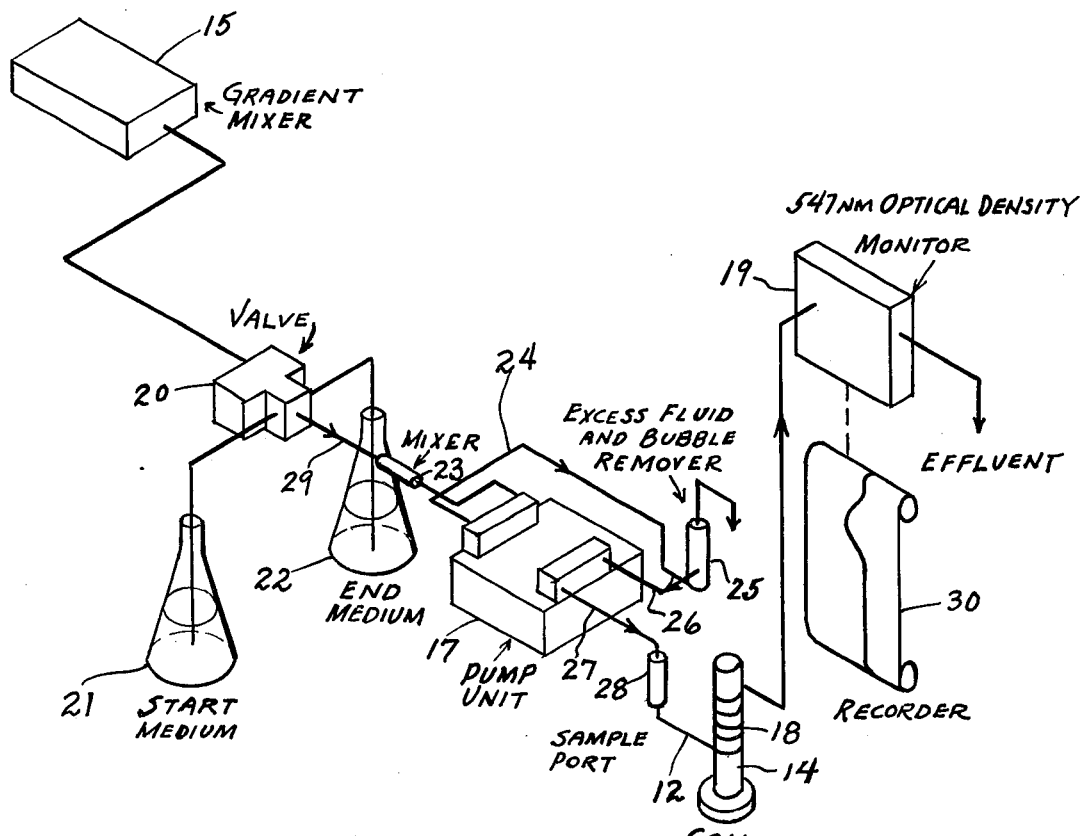

CAPILLARY FLOW METHOD AND APPARATUS FOR DETERMINATION OF CELL OSMOTIC FRAGILITY

FIELD OF THE INVENTION

This invention relates to techniques for the determination of cell osmotic fragility, and more particularly to a method and apparatus for obtaining a hemolysis curve of a blood sample by exposing the blood cells to a flow of a solution having a controlled variation of osmotic gradient.

BACKGROUND OF THE INVENTION

The osmotic fragility test of erythrocytes has been a relatively insignificant clinical test in medicine. The conventional Parpart method (see A. K. Parpart, P. B. Lorenz, E. R. Parpart, J. R. Greeg and A. M. Chase, "The Osmotic Resistance (Fragility) of Human Red Cells", J. Clin. Invest. 26:676, 1947 ) using multiple test tubes, is too cumbersome and time-consuming with respect to the value of the information derived from a few critical hemolysis points on an integrated curve.

In recent years, two improved methods have been reported which produce an entire hemolysis curve. The curve can be obtained with the method of Dannon (see D. Dannon: "A Rapid Micro Method for Recording Red Cell Osmotic Fragility by Continuous Decrease of Salt Concentration", J. Clin. Path 15:377, 1965 ) by subjecting cells to a gradual change of osmolarity by means of dialysis, while monitoring the change of transmittance of light through the solution. It uses a dialysis chamber equipped with a pair of celophane membranes to hold the sample solution. Dialysis through the membranes produces a gradual decrease of osmolarity in the sample solution. This osmotic gradient is a function of the distance between the two membranes and the integrity of the membranes itself. Therefore, slight disclocations and alterations of the membranes may affect the reproducibility of the results.

In the coil plant centrifuge technique (see R. Harada, Y. Ito, and E. Kimura: "A New Method of Osmotic Fragility Test of Erythrocytes with Coil Planet Centrifuge", Japanese J. of Phys. 19:306–314, 1969, and K. Katzimer and S. Shibata: "Coil Planet Centrifuge and its Application to the Observation of Altered Membrane Properties of Erythrocytes in Hepatobiliary Disorders", J. Lab. Clin. Med. 85: 855–864, 1975 ) a fine coiled tube is filled with a solution containing an accurate osmotic gradient. Blood cells introduced at the high osmolarity end of the coil move through the gradient solution at a predetermined rate determined by the slow rotation of the coil under the centrifugal force field. When the cells reach a critical portion of the gradient, they release the hemoglobin, which remains at this position within the coil, which then can be scanned along its length by means of a densitometer. One advantage of this method is that hemolysis takes place within a pure salt solution free from hemoglobin, since released hemoglobin is always left behind, and the intact cells are constantly washed with a new solution as they travel through the coil. Although this technique has advantages, it is rather cumbersome to use and is limited by the difficulties in accurate analysis of the hemolysis curve due to the poor optical properties of the tube wall.

For these reasons, most of the clinical laboratories are still using the conventional Parpart method for the osmotic fragility test of erythrocytes.

SUMMARY OF THE INVENTION

Accordingly, an object of the invention is to overcome the defects of the prior art, such as indicated above; another object is for improved osmotic fragility testing.

Yet another object is to provide a novel and improved technique for performing an osmotic fragility test for erythrocytes, employing the exposure of the cells to pure salt solution of continuously changing osmolarity in a system which is relatively simple, which is highly reproducible, and which provides highly accurate results.

A further object of the invention is to provide an improved method and apparatus for testing erythrocytes for osmotic fragility by exposing them to salt solution of continuously changing osmolarity, utilizing the Poiseuille parabolic flow pattern together with gravity to retain the cells in a long capillary tube while the solution of decreasing osmolarity is passed through the tube for hemolysis.

A still further object of the invention is to provide an improved method and apparatus for testing erythrocytes for osmotic fragility by exposing the cells to a flow of salt solution of continuously changing osmolarity, causing hemoglobin to be released therefrom and to be quickly removed by the axial flow pattern of the moving salt solution, and monitoring the output flow spectrophotometrically for recording and hemolysis curve.

BRIEF DESCRIPTION OF THE DRAWINGS

Further objects and advantages of the invention will become apparent from the following description and claims, and from the accompanying drawings of a preferred mbodiment, wherein:

FIGS. 1A, 1B and 1C are enlarged diagrammatic views of sections of capillary tubes having various orientations and showing the positions taken by red blood cells as a result of the Poiseuille's flow patterns in the tubes for the different orientations.

FIG. 2 is a schematic block diagram of a system for performing an osmotic fragility test of erythrocytes, employing the technique of the present invention.

DESCRIPTION OF A PREFERRED EMBODIMENT

Figure 3:
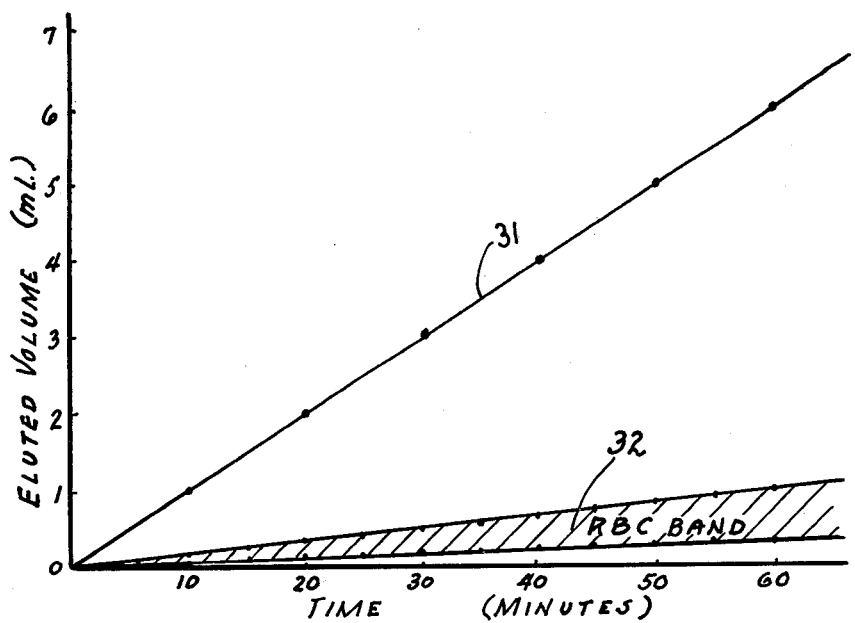
FIG. 3 is a graph showing the relative speed at which the salt solution and the red blood cells pass through the capillary tube coil in a system such as is illustrated in FIG. 2.

In the capillary flow method of the present invention, NaCl solution with a desired osmotic gradient is accurately prepared by means of a gradient mixer and is passed through an upstanding coiled capillary tube, namely, a coiled tube having a substantially vertical coil axis so that the individual turns thereof are nearly horizontal.

Referring to FIGS. 1A, 1B and 1C, the Poiseuille flow pattern through a capillary tube is represented by a parabolic curve 11, which expresses the fact that the drag force exerted by the fluid in the tube is a maximum at the tube axis and diminishes toward the tube inside wall surface. This curve also expresses the fact that the fluid stream located near the tube axis moves with a relatively high speed as compared with the fluid stream near the tube inside wall surface. It follows from this that particles which can be carried by the fluid streams, such as erythrocytes, will move similarly, namely, in accordance with the Poiseuille parabolic flow pattern and in accordance with their particular positioning along said flow pattern.

Thus, in FIG. 1A, the tube, shown at 12, is oriented vertically and the flow is downward. The flow drag forces will tend to herd the erythrocytes, shown at 13, toward the tube axis. The fluid will carry the erythrocytes near the tube axis with almost the same speed as the fluid itself, and will carrying the remainder at speeds in accordance with the locations of the erythrocytes along the parabolic Poiseuille's flow pattern 11. The same general result is obtained with the vertical tube orientation of FIG. 1B, but the flow is upward instead of downward.

In FIG. 1C the tube 12 is substantially horizontal, and gravitational force acts on the erythrocytes 13 and tends to cause them to lie on the bottom of the tube wall, namely, at a location along the Poiseuille's parabolic flow pattern where the flow speed is relatively low. Consequently, the flow speed of the erythrocytes is relatively low as compared with the average fluid flow speed through the tube, and the major portion of the moving fluid will flow past the erythrocytes with relatively high speed.

Thus, due to the Poiseuille's flow pattern, together with the gravitational effect, with an orientation similar to FIG. 1C, erythrocytes introduced into an upstanding capillary tube coil, as above mentioned, will move through the coil at a rate much slower than that of the gradient solution. Because of this, in accordance with the present invention, the cells are exposed to a gradual decrease in osmolarity for hemolysis. Hemoglobin released from the cells is then quickly removed by the flowing stream. Optical density is recorded against time, at 547 nm. The cells are being constantly washed and being exposed to a new portion of the gradient solution free from hemoglobin, but in contrast to the coil planet centrifuge technique, the released hemoglobin is monitored with a simple and refined optical system to record the entire hemolysis curve.

As previously stated, the method described herein utilizes the parabolic pattern of Poiseuille's flow and gravity in a horizontal fine tube to retain red blood cells while a desired gradient of saline solution is flowing through the tube. Also, as above pointed out, the velocity of the red blood cells varies with the orientation of the tube, i.e., in a vertically oriented tube where gravity acts along the length of the tube (see FIGS. 1A and 1B) the red blood cells will migrate towards the center of the Poiseuille's flow pattern, thereby attaining relatively high velocities. However, when the tube is in a nearly horizontal orientation with respect to gravity (see FIG. 1C) the red blood cells will move along the length of the tube at a much slower rate than the solution. Plasma, platelets, hemoglobin, and anything less affected by gravity flow rapidly through the tube. Therefore, an effective retention of the red blood cells can be achieved in a column by winding a small-diameter tube 12 around an upstanding cylindrical support, such as the cylindrical support shown diagrammatically at 14 in FIG. 2. The larger the diameter of the cylindrical support relative to the diameter of the tube 12, the more horizontal will be the flow. Consequently, a saline solution with a decreasing osmotic gradient introduced through the tubes elutes hemoglobin relased from hemolyzed cells while leaving intact cells within the column. A hemolysis curve is obtained by the continuous monitoring of the outlet flow of the column with a spectrophotometer.

FIG. 2 shows diagrammatically the basic elements of a system according to the present invention, said system comprising a gradient mixer 15, a pump unit 17 to provide the flow, a coil 18 of capillary tubing 12 to provide the retention of the red blood cells, and a detector 19 operating a recorder 30 to monitor the hemolysis of the cells.

The gradient mixer 15 may be similar to the LKB Ultrograd 11300, made by LKB Produkter Fabriksaktiebolag, Stockholm, Sweden, provided with a time-controlled dual valve unit 20 connected to vary the proportions of respective "start medium" and "end medium" liquid components admitted from flasks 21 and 22 to the fluid line 29 and furnished to a mixer 23 so as to deliver a gradient of 0.85 to 0 % NaCl over a period of 30 minutes.

The gradient solution is withdrawn from the mixer 23 by the first stage of a two-stage pump unit 17, which may comprise a Technicon Proportioning Pump, made by Technicon Chromatography Corp., New York, N.Y., through a length of 0.065 inch I.D. pump tubing 24 to a conventional bubble trap and excess fluid remover, shown at 25. A smaller-diameter length 26 of 0.015 inch I.D. tubing goes back through the second stage of pump unit 17. The exit line 27 of said second pump stage is connected with a well 28 provided with conventional means to inject the sample. The sample and gradient solution pass through the coil 18 and thence to the 547 nm optical density monitor unit 19, which may comprise an LKB Uvicord II detector and recorder (shown at 30), made by the aforesaid LKB Produkter Fabriksaktiebolag. The cell used in the Uvicord II detector is preferably a 1.8 mm I.D. flow cell with 547 nm interference filter for detection of hemoglobin.

In a typical system according to FIG. 2, a gradient rate of 0.85 to 0% NaCl for 30 minutes and a pump rate of 6.7 ml/hour were selected to provide proper mixing of the red blood cells with the solution and to allow the cells to be exposed to approximately a 0.03% change in NaCl gradient per minute. The rate of red blood cell travel was about 1/10 the rate of travel of the solution, or approximately 18 mm/minute.

In this typical system the coil 18 was a piece of 0.85 mm I.D. Teflon tubing 140 cm long, with a capacity of 0.8 ml. Larger diameter tubing gave insufficient washing of the blood cells with the flowing saline solution, this being manifested in unnecessary broadening of the hemolysis peak. In smaller diameter tubing mixing was too violent and carryover of the cells took place. The optimum length of the coil is determined by the flow rate and the gradient rate selected.

FIG. 3 graphically shows the difference in flow between the gradient solution (shown by the rate line 31) and the red blood cells (shown by the shaded area 32). The shaded area 32 indicates the spreading of the red blood cells along the tube as a function of time.

In a typical procedure the gradient solution preparation was as follows:

A stock solution of buffered sodium chloride osmotically equivalent to 10% NaCl was made as follows: 90 gms NaCl, 13.65 gms $Na_2HPO_4$ and 2.15 gms $NaH_2PO_4 \cdot H_2O$ were dissolved in distilled water and the final volume was adjusted to 1 liter. The "start medium" solution, equivalent to 0.85% NaCl, was prepared by diluting 85 ml of the stock solution with distilled water to bring the final volume to 1 liter. This final solution had a pH of 7.4. Distilled water was used as the "end medium" solution. The linear gradient between starting and ending solutions was obtained with the LKB Ultrograd 11300 with a 30-minute time scan.

The actual tests were performed as follows: The sample port 28 was opened and the pump unit 17 was operated for about 1 minute on rapid wash cycle so that the pump tubing was flushed with the starting solution. A syringe containing some starting solution (about 3cc) was used to flush through the detector 19 and coil 18 from the elution end to the sample port 28, where excess was removed with a vacuum probe. The sample was then introduced into the sample port and the port closed. The pump unit 17 and gradient mixer 15 were then started simultaneously with the recorder 30.

Undiluted blood specimens treated with heparin or EDTA were used as samples and injected with a micropipet or a Hamilton 10 microliter syringe. In the typical studies made, both heparin and EDTA-treated blood gave the same results. This is probably due to the fact that these anti-coagulants were immediately washed away by the buffered gradient solution.

A calibration of % NaCl vs. time was made on the recorder 30 using a conventional precalibrated conductivity meter. This is shown at 33 in FIG. 4.

Figure 4:
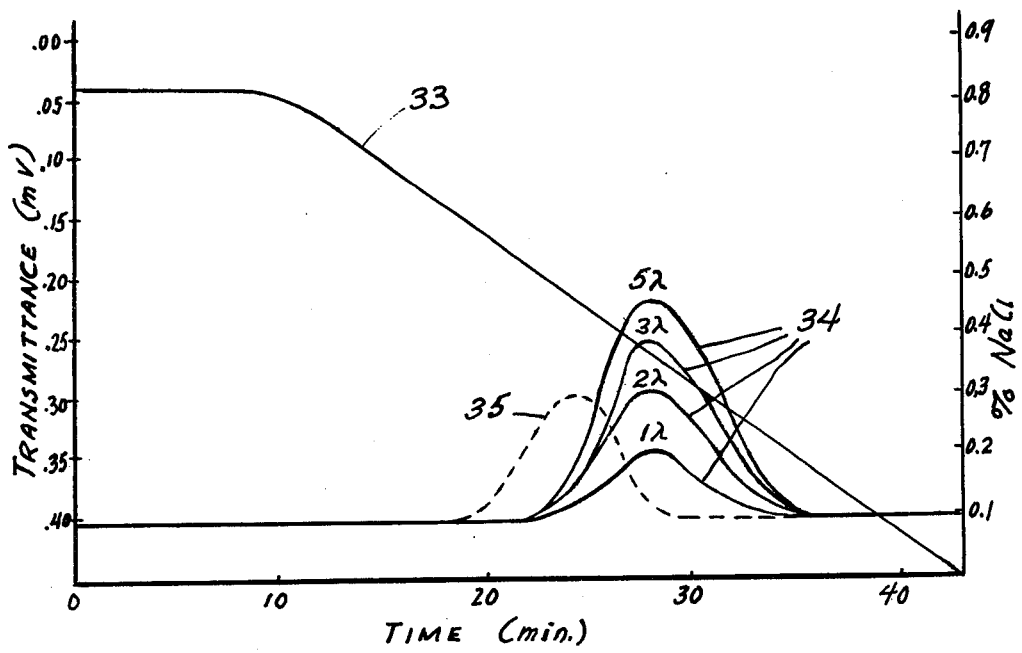
FIG. 4 is a graph showing typical hemolysis curves obtained for four different blood sample doses from a normal individual, employing the method and apparatus of the present invention, with the % NaCl calibration linear with respect to time.

FIG. 4 also shows hemolysis response curves at 34 representing the responses for four different sample doses from the same normal patient. The curves 34 were obtained from fresh samples. Curves obtained from incubated normal samples would be shifted to the left, for example, as shown by the dotted curve 35, indicating increased osmotic fragility.

Abnormal samples would show characteristic osmotic fragilities, both with regard to fresh samples and incubated samples. A shift to the left, relative to a normal sample, would indicate increased osmotic fragility, whereas a shift to the right would indicate a decrease in osmotic fragility.

In some types of abnormal samples the recorded curve may show two distinct populations of cells, one of which decreases in osmotic fragility as the other increases, for example after incubation.

In a sample where sickle cell anemia was present, the recorded curves showed low osmotic fragility in both fresh and incubated samples, but in this case the whole cell population had become more fragile upon incubation, similar to the results with a normal sample.

From investigations made using the technique of the present invention, it has been found that abnormalities can be defined by either noting the shape of the hemolysis curve or by relating the peaks and the end points.

As previously mentioned, the technique of the present invention provides more accurate results than the Parpart method, since the integrated curve obtained by the Parpart method is based on a line connecting four or five points between the end points of hemolysis and a reading of the 50% hemolysis point taken from this. On the other hand, the curve obtained with a gradually changing gradient, as in the technique of the present invention, does not have the inherent inaccuracies of a small number of reading, but is amenable to further analysis.

From investigations made with the technique of the present invention, it has also been found that the results are highly reproducible, and that deviations are appreciably less than with the Parpart method. Also, the directly recorded curves provide valuable information, especially when dealing with abnormal samples that have more than one population of red blood cells, as above mentioned. In these instances (where the patient exhibits at least two separate populations of red blood cells after incubation) since the area under the curve is nearly proportional to hemoglobin content, the peak and end points will define the variances of symmetry of the curve, which in turn define the population distribution within the total red blood sample. The Parpart method would not be as effective in showing changes in symmetry and shifts in population distribution.

As above mentioned, the technique of the present invention does not rely upon maintaining the integrity of dialysis membranes, as in the method of Dannon, and does not present the optical monitoring difficulties of the coil planet centrifuge technique. In addition to overcoming these disadvantages, the technique of the present invention offers the following additional advantages: (1) the required sample size is small, (2) the output is in a non-integrated form, (3) there is no sample preparation necessary, (4) the accuracy and reproducibility are high, (5) the system is very amenable to the changing of parameters such as shape and slope of the gradient flow rate, temperature, monitoring wavelength, etc., for the study of osmotic fragility in other types of cells, (6) the system is also adaptable to automating for many samples simultaneously and/or successively, and (7) the eluent can be fractionated for further analysis.

Other possible applications include: (a) utilization of a computer for the determination of 50%, peak and end points, and the shapes of the integrated curves; (b) varying the gradient in a sawtooth manner to facilitate separation of the various populations in a group of red blood cells; (c) determination of the correlation between osmotic fragility and the age of the red blood cells; (d) determining the alterations in osmotic fragility due to the storage of blood; and (e) investigation of sickle cell anemia red blood cells that have been fractionated by density gradient centrifugation.

Although certain specific embodiments of an improved method and apparatus for the determination of cell osmotic fragility by a capillary flow technique have been disclosed in the foregoing description, it will be understood that various modifications within the spirit of the invention may occur to those skilled in the art. Therefore it is intended that the invention is not limited to the embodiment disclosed which is offered illustratively and that modifications and adaptations may be made without departing from the invention.

For example this method can be applied to other types of cells such as, leukocytes to hemolyze in a gradient solution and detected at 280 mm or other wavelengths or it can be utilized for hemolyzing different types of cells in other types of gradient solutions such as salt and detergent. The gradient solution can be of other forms such as exponential rather than linear. What is claimed is:

1. A method for determining cell osmotic fragility of a cell-containing sample comprising passing a salt solution through a capillary tube with substantially horizontal portions and wherein the flow follows Poiseuille's parabolic flow pattern, changing the osmotic gradient of the salt solution with time as it is passed through the capillary tube, inserting the sample in the tube so that it reaches said substantially horizontal portions, whereby the salt solution flows faster than the cells of the sample at said substantially horizontal portions and whereby the cells are exposed to salt solution of changing osmolarity, and continuously plotting the variation of optical density with time of the effluent from the capillary tube.

2. The method of claim 1, and wherein said capillary tube substantially horizontal portions comprise the turns of a vertically positioned capillary tube coil.

3. The method of claim 1, and wherein the change with time of said osmotic gradient is a substantially linear decrease.

4. The method of claim 1, and wherein said salt solution comprises an aqueous solution of sodium chloride.

5. The method of claim 1, and wherein the variation of optical density of the effluent is plotted at a transmission wavelength of approximately 547 nm.

6. The method of claim 1, and wherein the salt solution comprises an aqueous solution of sodium chloride and the gradient rate of change is approximately 0.85 to 0% NaCl for 30 minutes.

7. The method of claim 6, and wherein the flow rate of the sodium chloride solution through the capillary tube is approximately 6.7 ml/hour, with a tube inside diameter of approximately 0.85 mm.

8. An apparatus for the determination of cell osmotic fragility of a cell-containing sample comprising a source of salt solution, means to change the osmotic gradient of said salt solution over a period of time, a coiled capillary tube positioned with its axis substantially vertical, means to pump the salt solution of changing osmotic gradient from said source through said coiled capillary tube, means to admit the sample into the coiled capillary tube, whereby cells are substantially retained at the turns of the tube and the salt solution travels past the cells, and means to continuously measure the optical density of the effluent from said coiled capillary tube over said period of time.

9. The apparatus of claim 8, and wherein the salt solution comprises an aqueous solution of sodium chloride.

10. The apparatus of claim 9, and means to measure said optical density continuously at a wavelength of approximately 547 nm over said period of time, whereby to derive a hemolysis curve for a blood sample.

11. The apparatus of claim 8, and wherein said source of salt solution and the means to change the osmotic gradient of said salt solution and the means to change the osmotic gradient of said salt solution comprises a first receptacle containing a solution of sodium chlorine, a second receptacle containing water, a proportion-changing gradient mixer with a dual mixing valve assembly controlled by said gradient mixer, and conduit means connecting the respective receptacles to the inlets of said dual valve assembly, said dual valve assembly having a common outlet including a mixer for the changing proportions of sodium chloride solution and water.

12. The apparatus of claim 11, and wherein the means to admit the sample into the coiled capillary tube comprises a sample port connected between the outlet of said pump means and said coiled capillary tube.

13. The apparatus of claim 12, and wherein said coiled capillary tube is provided with a vertical upstanding cylindrical support member on which the capillary tube is wound.

* * * * *